US009289592B2

(12) United States Patent
Chinn et al.

(10) Patent No.: US 9,289,592 B2
(45) Date of Patent: Mar. 22, 2016

(54) SYSTEMS, APPARATUSES, AND METHODS FOR DIFFERENTIATING BETWEEN MULTIPLE LEADS IMPLANTED WITHIN A PATIENT

(75) Inventors: Kenny Kinyen Chinn, Castaic, CA (US); Michael A. Moffitt, Valencia, CA (US); Paul M. Meadows, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1341 days.

(21) Appl. No.: 12/400,260

(22) Filed: Mar. 9, 2009

(65) Prior Publication Data

US 2009/0234427 A1 Sep. 17, 2009

Related U.S. Application Data

(60) Provisional application No. 61/035,540, filed on Mar. 11, 2008.

(51) Int. Cl.
| | |
|---|---|
| *A61N 1/05* | (2006.01) |
| *A61B 17/32* | (2006.01) |
| *A61N 1/375* | (2006.01) |
| *A61N 1/372* | (2006.01) |

(52) U.S. Cl.
CPC ....... *A61N 1/05* (2013.01); *A61B 2017/320056* (2013.01); *A61N 1/372* (2013.01); *A61N 1/3752* (2013.01)

(58) Field of Classification Search
CPC ....... A61N 1/05; A61N 1/3752; A61N 1/372; A61B 2017/320056

USPC ......... 607/119, 122, 36, 129–131, 33, 35, 37, 607/116–117; 606/129–130, 108
See application file for complete search history.

(56) References Cited

U.S. PATENT DOCUMENTS

| | | | |
|---|---|---|---|
| 4,280,510 A | * | 7/1981 | O'Neill ................... 607/131 |
| 5,143,539 A | | 9/1992 | Lovell |
| 5,143,540 A | | 9/1992 | Pyzik et al. |
| 5,218,959 A | * | 6/1993 | Fenster ..................... 607/36 |
| 5,312,439 A | | 5/1994 | Loeb |
| 6,051,017 A | | 4/2000 | Loeb et al. |
| 6,164,284 A | | 12/2000 | Schulman et al. |

(Continued)

FOREIGN PATENT DOCUMENTS

| | | |
|---|---|---|
| WO | 03035173 A1 | 5/2003 |
| WO | 2005028025 A1 | 3/2005 |

(Continued)

*Primary Examiner* — Catherine Voorhees
(74) *Attorney, Agent, or Firm* — Lowe Graham Jones PLLC; Bruce E. Black

(57) ABSTRACT

Systems, apparatuses, and methods for differentiating between multiple leads that are implanted within a patient include a stimulator configured to be implanted at an implant site within the patient and generate electrical stimulation current, a plurality of leads each comprising one or more electrodes configured to deliver the electrical stimulation current at a stimulation site within the patient, and a shuttle assembly having a plurality of receiving ports each configured to receive a proximal portion of one of the leads and guide the leads from the stimulation site to the implant site of the stimulator. The shuttle assembly is configured to enable a user to differentiate between each of the leads after the leads are guided to the implant site of the stimulator.

21 Claims, 10 Drawing Sheets

(56) References Cited

U.S. PATENT DOCUMENTS

| | | |
|---|---|---|
| 6,185,452 B1 | 2/2001 | Schulman et al. |
| 6,208,894 B1 | 3/2001 | Schulman et al. |
| 6,381,496 B1 * | 4/2002 | Meadows et al. ............... 607/59 |
| 6,553,263 B1 | 4/2003 | Meadows et al. |
| 6,760,626 B1 | 7/2004 | Boveja |
| 7,912,557 B1 * | 3/2011 | Randle et al. ................. 607/119 |
| 2001/0032023 A1 * | 10/2001 | Herweck et al. ........... 623/23.72 |
| 2003/0040784 A1 | 2/2003 | Pasternak et al. |
| 2003/0077943 A1 | 4/2003 | Osypka |
| 2003/0100220 A1 * | 5/2003 | Scheiner ...................... 439/491 |
| 2004/0059348 A1 | 3/2004 | Geske et al. |
| 2004/0260370 A1 * | 12/2004 | Ley et al. ...................... 607/115 |
| 2006/0089697 A1 * | 4/2006 | Cross et al. ................... 607/122 |
| 2006/0089698 A1 * | 4/2006 | Sundberg et al. ............. 607/122 |
| 2006/0206184 A1 * | 9/2006 | Tockman et al. ............. 607/122 |
| 2006/0247751 A1 * | 11/2006 | Seifert ......................... 607/122 |
| 2007/0282411 A1 | 12/2007 | Franz et al. |
| 2008/0046062 A1 * | 2/2008 | Camps et al. ................ 607/133 |

FOREIGN PATENT DOCUMENTS

| | | |
|---|---|---|
| WO | 2007115198 A2 | 10/2007 |
| WO | 2008017059 A1 | 2/2008 |

* cited by examiner

US 9,289,592 B2

SYSTEMS, APPARATUSES, AND METHODS FOR DIFFERENTIATING BETWEEN MULTIPLE LEADS IMPLANTED WITHIN A PATIENT

CROSS REFERENCE TO RELATED APPLICATIONS

This application claims the benefit of U.S. Provisional Patent Application Ser. No. 61/035,540, filed Mar. 11, 2008, the entire contents of which is incorporated herein by reference.

BACKGROUND

An implantable stimulator is used to treat a variety of medical disorders by providing electrical stimulation pulses via one or more electrodes placed at a desired stimulation site within a patient. The electrodes are typically disposed on one or more leads that are coupled to the implantable stimulator.

In some configurations, the portion of the leads with the electrodes disposed thereon are implanted at the desired stimulation site while the stimulator is implanted at a more surgically convenient location (e.g., a subcutaneous pocket formed within the torso of a patient). The one or more leads may then be tunneled from the stimulation site to the implant site and coupled to the implanted stimulator.

In many instances, a plurality of leads is used in conjunction with an implantable stimulator. Each lead may have a number of electrodes disposed thereon. For example, an exemplary configuration includes three leads each with eight electrodes disposed thereon. In this manner, electrical stimulation may be applied by the stimulator to the stimulation site via one or more of twenty-four different electrodes.

However it is often difficult for physicians to differentiate between multiple leads after they have been tunneled from the stimulation site to the implanted stimulator. Some physicians have been known to tie one more sutures around one or more of the leads to differentiate each lead from the others. However, such a solution is cumbersome, time consuming, and prone to errors.

SUMMARY

Systems for differentiating between multiple leads that are implanted within a patient include a stimulator configured to be implanted at an implant site within the patient and generate electrical stimulation current, a plurality of leads each comprising one or more electrodes configured to deliver the electrical stimulation current at a stimulation site within the patient, and a shuttle assembly having a plurality of receiving ports each configured to receive a proximal portion of one of the leads and guide the leads from the stimulation site to the implant site of the stimulator. The shuttle assembly is configured to enable a user to differentiate between each of the leads after the leads are guided to the implant site of the stimulator.

Apparatuses for differentiating between multiple leads that are implanted within a patient include an elongated body configured to be guided from a stimulation site to an implant site of a stimulator within a patient, a plurality of receiving ports disposed on the elongated body and each configured to receive a proximal portion of an electrode lead, and at least one identifying mark configured to enable a user to differentiate between each of the leads after the elongated body is guided from the stimulation site to the implant site.

Methods of differentiating between multiple leads that are implanted within a patient include implanting a stimulator configured to generate electrical stimulation current at an implant site within a patient, providing a plurality of leads each having at least one electrode disposed on a distal portion thereof and configured to deliver the electrical stimulation current to a stimulation site within the patient, positioning the distal portions of the leads at the stimulation site, coupling a proximal portion of the leads to a shuttle assembly, and guiding the shuttle assembly from the stimulation site to the implant site of the stimulator.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

DETAILED DESCRIPTION

Systems, apparatuses, and methods for differentiating between multiple leads that are implanted within a patient are described herein. A stimulator may be implanted at an implant site within the patient and configured to generate electrical stimulation current. A plurality of leads each comprising one or more electrodes may be provided and configured to deliver the electrical stimulation current at a stimulation site within the patient. A shuttle assembly may receive a proximal portion of each of the leads with corresponding receiving ports and guide the leads from the stimulation site to the implant site of the stimulator. As will be described in more detail below, the shuttle assembly is configured to enable a user to differentiate between each of the leads after the leads are guided from the stimulation site to the implant site of the stimulator.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Figure 1:
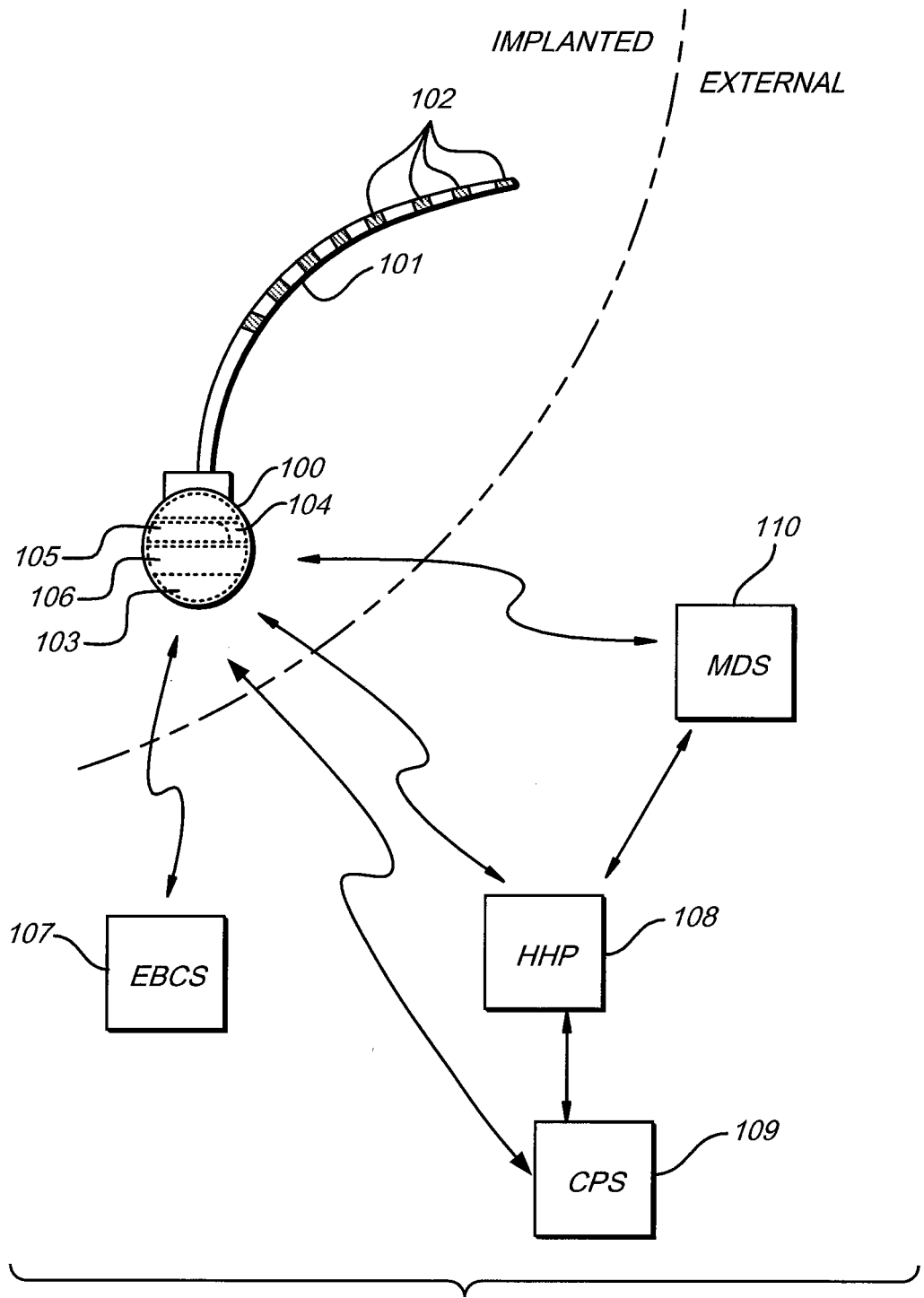
FIG. 1 illustrates an exemplary stimulator that may be used to apply electrical stimulation to one or more stimulation sites within a patient according to principles described herein.

To facilitate an understanding of the systems and methods described herein, a more detailed description of an implantable stimulator and its operation will now be given. FIG. 1 illustrates an exemplary stimulator 100 that may be used to apply electrical stimulation to one or more stimulation sites within a patient. The stimulation site may include any nerve or other tissue within the patient such as, but not limited to, one or more neural elements within the spinal cord region.

In some examples, the exemplary stimulator 100 shown in FIG. 1 may include at least one lead 101 coupled thereto. In some examples, the at least one lead 101 includes a number of electrodes 102 through which electrical stimulation current may be applied at one or more stimulation sites. It will be recognized that the at least one lead 101 may include any number of electrodes 102 arranged in any configuration as best serves a particular application.

For example, the at least one lead 101 may include a plurality of leads 101 each with one or more electrodes 102 disposed thereon. To illustrate, an exemplary configuration includes three leads each with eight electrodes disposed thereon. In this manner, electrical stimulation may be applied by the stimulator 100 to one or more stimulation sites via one or more of twenty-four different electrodes. It will be recognized that the stimulator 100 may be coupled to any number of leads 101 and that each lead 101 may include any number of electrodes 102 as may serve a particular application.

In some examples, the stimulator 100 may additionally or alternatively be coupled to one or more catheters (not shown) through which one or more therapeutic drugs may be applied to one or more stimulation sites.

As illustrated in FIG. 1, the stimulator 100 includes a number of components. For example, the stimulator 100 may include a power source 103, a coil 104, electrical circuitry 105, and/or a programmable memory unit 106. It will be recognized that the stimulator 100 may include additional and/or alternative components as best serves a particular application.

The power source 103 is configured to output current used to supply the various components within the stimulator 100 with power and/or to generate the power used for electrical stimulation. The power source 103 may include a primary battery, a rechargeable battery (e.g., a lithium-ion battery), a super capacitor, a nuclear battery, a mechanical resonator, an infrared collector (receiving, e.g., infrared energy through the skin), a thermally-powered energy source (where, e.g., memory-shaped alloys exposed to a minimal temperature difference generate power), a flexural powered energy source (where a flexible section subject to flexural forces is part of the stimulator), a bioenergy power source (where a chemical reaction provides an energy source), a fuel cell, a bioelectrical cell (where two or more electrodes use tissue-generated potentials and currents to capture energy and convert it to useable power), or the like.

The stimulator 100 may also include a coil 104 configured to receive and/or emit a magnetic field (also referred to as a radio frequency (RF) field) that is used to communicate with, or receive power from, one or more external devices. Such communication and/or power transfer may include, but is not limited to, transcutaneously receiving data from the external device, transmitting data to the external device, and/or receiving power used to recharge the power source 103.

For example, an external battery charging system (EBCS) 107 may be provided to generate power that is used to recharge the power source 103 via any suitable communication link. Additional external devices including, but not limited to, a hand held programmer (HHP) 108, a clinician programming system (CPS) 109, and/or a manufacturing and diagnostic system (MDS) 110 may also be provided and configured to activate, deactivate, program, and/or test the stimulator 100 via one or more communication links. It will be recognized that the communication links shown in FIG. 1 may each include any type of link used to transmit data or energy, such as, but not limited to, an RF link, an infrared (IR) link, an optical link, a thermal link, or any other energy-coupling link.

Additionally, if multiple external devices are used in the treatment of a patient, there may be communication among those external devices, as well as with the implanted stimulator 100. It will be recognized that any suitable communication link may be used among the various devices illustrated.

The external devices shown in FIG. 1 are merely illustrative of the many different external devices that may be used in connection with the stimulator 100. Furthermore, it will be recognized that the functions performed by any two or more of the external devices shown in FIG. 1 may be performed by a single external device.

The stimulator 100 may also include electrical circuitry 105 configured to generate the electrical stimulation current that is delivered to the damaged neural tissue via one or more of the electrodes 102. For example, the electrical circuitry 105 may include one or more processors, capacitors, integrated circuits, resistors, coils, and/or any other component configured to generate electrical stimulation current.

The stimulator 100 may also include a programmable memory unit 106 configured to store one or more stimulation parameters. The programmable memory unit 106 allows a patient, clinician, or other user of the stimulator 100 to adjust the stimulation parameters such that the stimulation applied by the stimulator 100 is safe and effective in treating a particular patient. The programmable memory unit 106 may include any type of memory unit such as, but not limited to, random access memory (RAM), static RAM (SRAM), a hard drive, or the like.

The stimulator 100 of FIG. 1 is illustrative of many types of stimulators that may be used in accordance with the systems and methods described herein. For example, the stimulator 100 may include an implantable pulse generator (IPG), a microstimulator, an external trial stimulator, or any other type of device configured to deliver electrical stimulation to a stimulation site within a patient. Exemplary IPGs suitable for use as described herein include, but are not limited to, those disclosed in U.S. Pat. Nos. 6,381,496; 6,553,263; and 6,760, 626. Exemplary microstimulators suitable for use as described herein include, but are not limited to, those disclosed in U.S. Pat. Nos. 5,143,539; 5,143,540; 5,312,439;

6,185,452; 6,164,284; 6,208,894; and 6,051,017. All of these listed patents are incorporated herein by reference in their respective entireties.

The stimulator 100 is often implanted at a surgically convenient location (e.g., within a subcutaneous pocket created in the torso). However, the stimulation site is often located relatively far away from the implant location of the stimulator 100. For example, the stimulation site may be located within the brain, the epidural space of the spinal cord, near a peripheral nerve, or at any other suitable location.

Because the stimulation site is often located relatively far away from the implant location of the stimulator 100, the one or more leads 101 that are used to facilitate stimulation of the stimulation site are often tunneled from the stimulation site to the implant site of the stimulator 100. To this end, a physician often inserts a tunneling straw within the patient that runs from the stimulation site to the implant site of the stimulator 100. The tunneling straw may include a lumen extending therethrough through which the one or more leads 101 may be guided from the stimulation site to the implant site of the stimulator 100.

However, it is often difficult for physicians to differentiate between multiple leads after they have been tunneled from the stimulation site to the implant site of the stimulator 100. Some physicians have been known to tie one or more sutures around one or more of the leads before they are inserted into the tunneling straw to differentiate each lead from the others after they exit the tunneling straw. However, such a solution is cumbersome, time consuming, and prone to errors. Hence, the systems and methods described herein may be used to facilitate differentiation of leads once they have been tunneled from a stimulation site to the implant site of the stimulator 100.

In some examples, a shuttle assembly may be used to facilitate differentiation of one or more leads 101 that have been tunneled from a stimulation site to the implant site of the stimulator 100.

Figure 2:
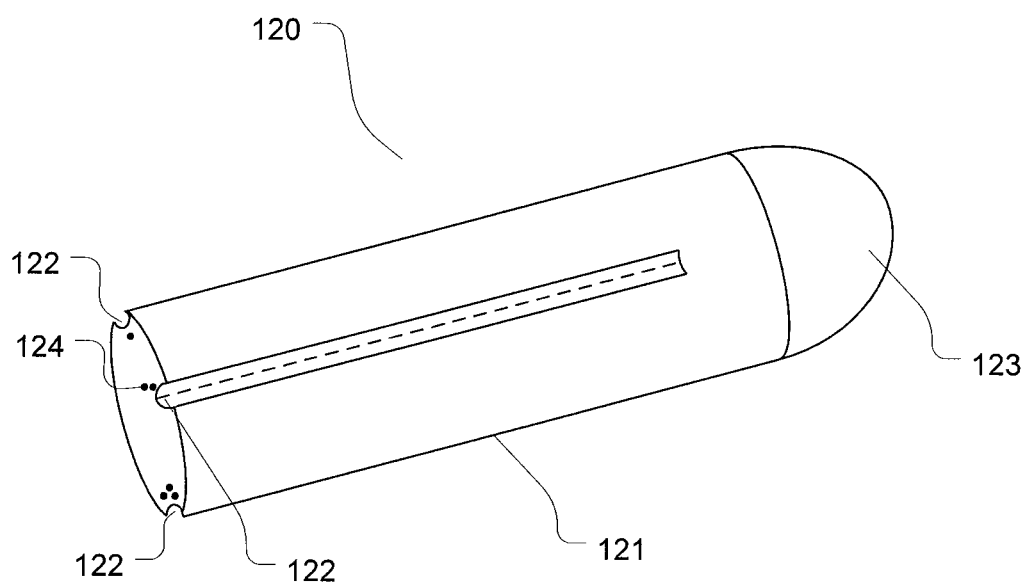
FIG. 2 is a perspective view of an exemplary shuttle assembly according to principles described herein.

FIG. 2 is a perspective view of an exemplary shuttle assembly 120. As shown in FIG. 2, the shuttle assembly 120 may include an elongated body 121 with one or more tapered ends 123. The tapered ends 123 may be configured to facilitate insertion of the shuttle assembly 120 into a tunneling straw, as will be described in more detail below. Once the shuttle assembly 120 has been inserted into the tunneling straw, the elongated body 121 may prevent the shuttle assembly 120 from flipping or rotating therein.

The shuttle assembly 120 may be made out of any suitable material as may serve a particular application. For example, the shuttle assembly 120 may be made out of a suitable plastic, polymer, metal, or any other material shown to be suitable for surgical procedures.

As shown in FIG. 2, the exemplary shuttle assembly 120 may include a plurality of receiving ports 122 disposed thereon. In some examples, the ports 122 may be configured to receive proximal portions of one or more leads 101. In this manner, as will be described in more detail below, the leads 101 may be removably coupled to the ports 122 prior to being tunneled to the implant site of the stimulator 100. The shuttle assembly 120 may then be tunneled from the stimulation site to the implant site of the stimulator 100. By noting which lead was inserted into which port 122, a surgeon or other user may differentiate the leads 101 as they are removed from the shuttle assembly 120 after the shuttle assembly 120 is tunneled to the implant site of the stimulator 100.

Figure 3A:
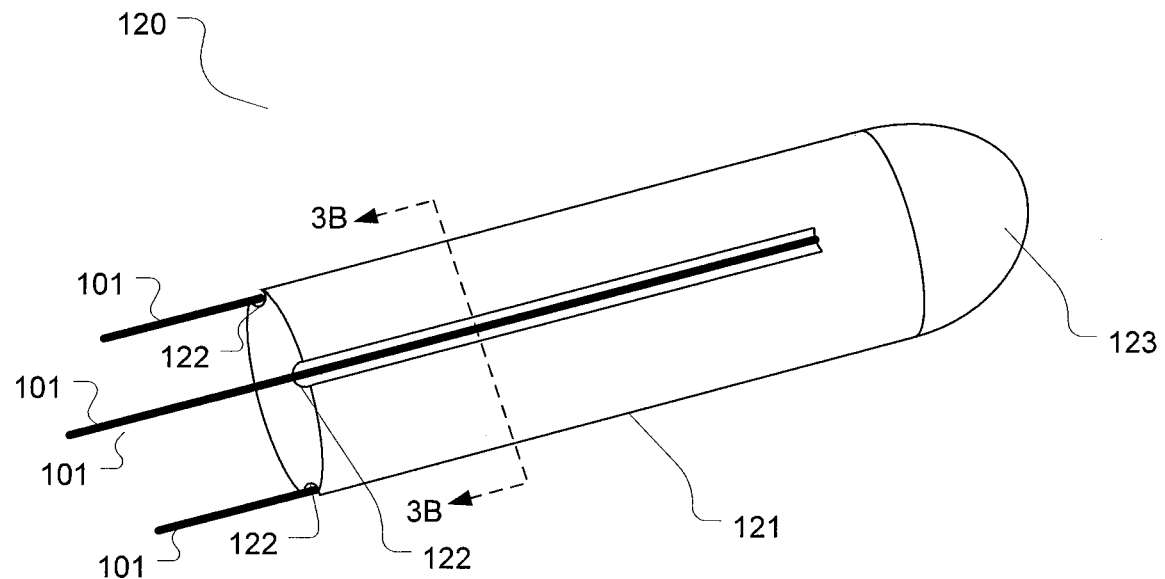
FIG. 3A shows leads loaded in an exemplary shuttle according to principles described herein.
Figure 3B:
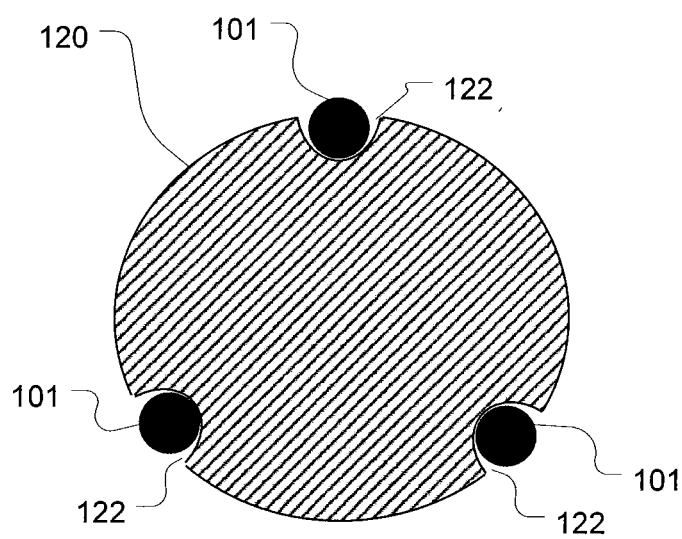
FIG. 3B is a cross-sectional view of the shuttle assembly taken along the perspective line indicated in FIG. 3A according to principles described herein.

The ports 122 may include any coupling means configured to couple the leads 101 to the shuttle assembly 120. For example, the ports 122 may include one or more grooves each configured to receive a lead 101. To illustrate, FIG. 3A shows the shuttle assembly 120 with a number of leads 101 inserted into corresponding ports 122 configured as grooves. FIG. 3B is a cross-sectional view of the shuttle assembly 120 taken along the perspective line indicated in FIG. 3A. In some examples, the leads 101 may be snapped or otherwise inserted into the ports 122. After the leads 101 have been inserted into the ports 122, as will be described in more detail below, the shuttle assembly 120 may be inserted into a tunneling straw and guided to the implant site of the stimulator 100. A physician may then remove the leads 101 from the shuttle assembly 120 and couple the leads to the stimulator 100.

It will be recognized that the ports 122 may include additional or alternative coupling means as may serve a particular application. For example, one or more of the ports 122 may additionally or alternatively include an adhesive, a clamping device, a staple, a pin, or any other coupling device or means configured to removably couple the leads 101 to the shuttle assembly 120.

Returning to FIG. 2, the shuttle assembly 120 may include one or more identifying marks 124 configured to facilitate differentiation of the leads 101 after they have been coupled to the ports 122. For example, each mark 124 may be associated with one of the ports 122 and may be located in any suitable location on the shuttle assembly 120. To illustrate, the marks 124 are located adjacent to each of the ports 122 in FIG. 2.

Hence, after the leads 101 have been coupled to the ports 122 of the shuttle assembly 120, the shuttle assembly 120 may be tunneled from the stimulation site to the implant site of the stimulator 100. Because each port 122 includes an associated identifying mark 124, the leads 101 may more easily be identified and distinguished one from another as they are removed from the shuttle assembly 120. The leads 101 may then be appropriately coupled to the stimulator 100.

It will be recognized that the identifying marks 124 may include any suitable label or marking configured to differentiate the ports 122 one from another. For example, the identifying marks 124 may include, but are not limited to, one or more colors, numbers, dots, stamps, ink, laser etchings, and/or any other suitable mark. In some alternative examples, the ports 122 may be of varying length or dimension to facilitate differentiation of leads 101 that are coupled thereto.

Figure 4:
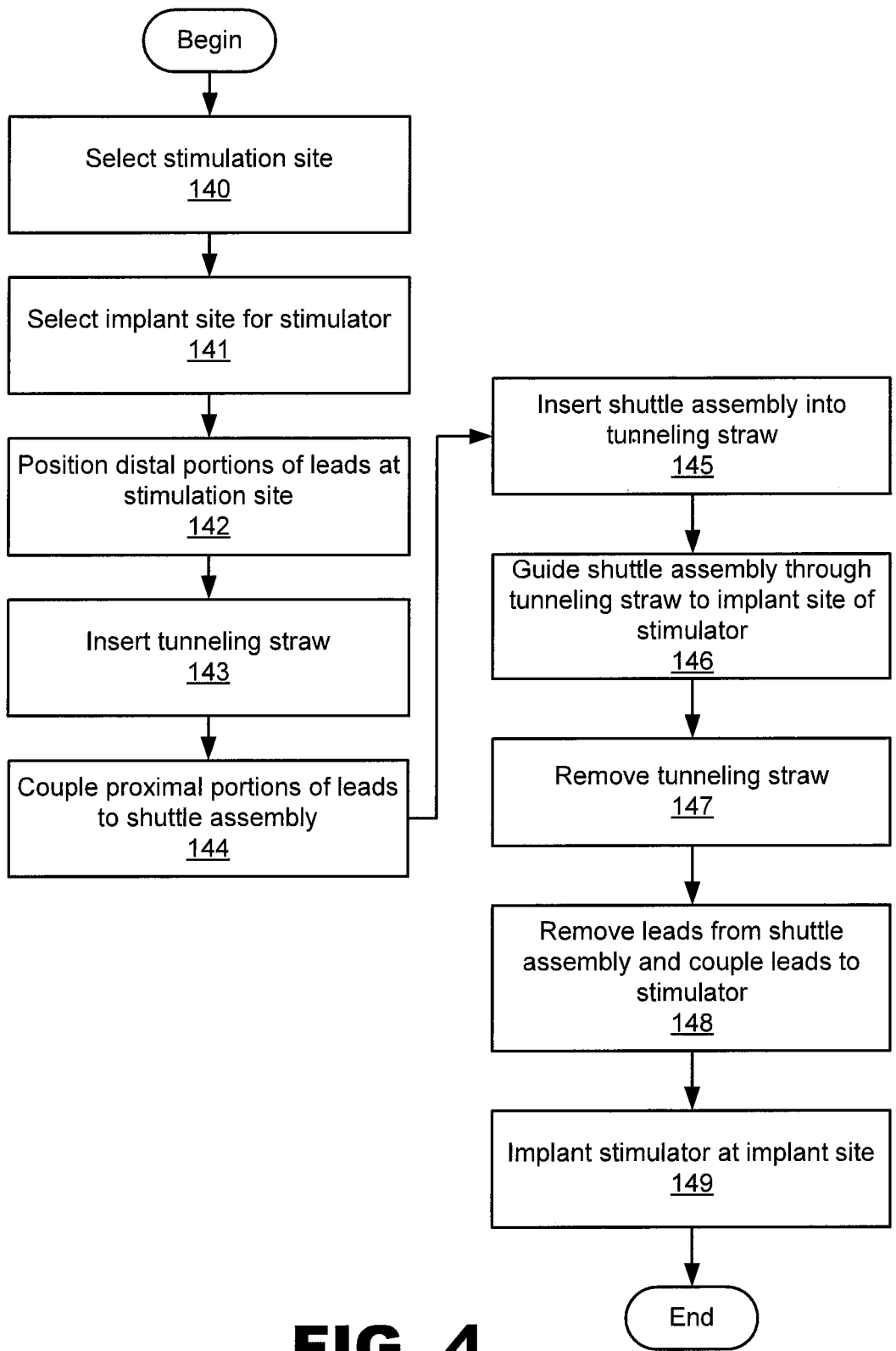
FIG. 4 is a flow chart illustrating an exemplary method of facilitating lead identification with a shuttle assembly according to principles described herein.

FIG. 4 is a flow chart illustrating an exemplary method of facilitating lead differentiation with a shuttle assembly. While FIG. 4 illustrates exemplary steps according to one embodiment, other embodiments may omit, add to, reorder, and/or modify any of the steps shown in FIG. 4.

In step 140, a stimulation site within a patient is selected. For example, the stimulation site may be located within the brain, the epidural space of the spinal cord, near a peripheral nerve, or at any other suitable location. An entrance cut may be made through the skin of the patient (e.g., with a scalpel) at a location that enables the surgeon to place stimulating leads at the stimulation site.

In step 141, an implant site for a stimulator is selected. The implant site may include any site within the patient as may serve a particular application. For example, the implant site may include a subcutaneous pocket created in the torso of the patient or any other surgically convenient location. An exit cut may be made through the skin of the patient at a location that enables the surgeon to placed the stimulator at the implant site.

In step 142, distal portions of the leads are positioned at the stimulation site such that the electrodes that are disposed thereon are in communication with the stimulation site. As used herein, the term "in communication with" refers to the electrodes being adjacent to, in the general vicinity of, in close proximity to, directly next to, or directly on the stimulation site.

In step 143, a tunneling straw is inserted within the patient using a tunneling rod or other suitable device. The tunneling straw runs from the stimulation site to the implant site of the stimulator. The tunneling straw may be inserted within a tunnel created by a tunneling rod, for example.

In step 144, proximal portions of a plurality of electrode leads are coupled to a shuttle assembly. The proximal portions of the leads may be coupled to the shuttle assembly in any of the ways described herein. For example, each lead may be coupled to a distinct port that is a part of the shuttle assembly.

Figure 5:
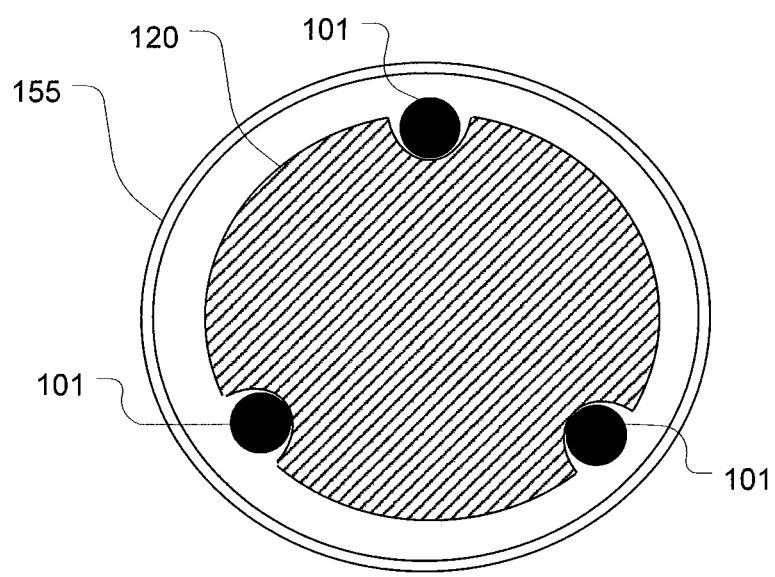
FIG. 5 is a cross-sectional view of the shuttle assembly after it has been inserted within a tunneling straw according to principles described herein.

In step 145, the shuttle assembly is inserted into the end of the tunneling straw that is closest to the stimulation site. To illustrate, FIG. 5 is a cross-sectional view of the shuttle assembly 120 after it has been inserted within a tunneling straw 155. As shown in FIG. 5, the diameter of the shuttle assembly 120 may be slightly smaller than the diameter of the tunneling straw 155. In this manner, the shuttle assembly 120 may be prevented from flipping within the straw 155 while it is being guided through the tunneling straw 155 to the implant site of the stimulator 100.

Returning to FIG. 4, the shuttle assembly is guided through the tunneling straw to the implant site of the stimulator, as shown in step 146. In some examples, an elongated rod or other device may be used to push the shuttle assembly through the tunneling straw from the stimulation site to the implant site of the stimulator. Additionally or alternatively the shuttle assembly may be pulled through the tunneling straw.

In step 147, the tunneling straw is removed from the patient. For example, the tunneling straw may be pulled back through the tunnel over the leads and shuttle.

In step 148, the leads are removed from the shuttle assembly and coupled to the stimulator. In some examples, the leads are removed from the shuttle assembly and coupled to the stimulator one at a time. In this manner, a surgeon or other user may differentiate the leads one from another as they are removed from the shuttle assembly by noting the identifying marks that are a part of the shuttle assembly.

In step 149, the stimulator is implanted at the selected implant site. Any suitable method of implantation may be used as may serve a particular application. The stimulator may then apply electrical stimulation at the stimulation site via one or more of the leads.

Figure 6A:
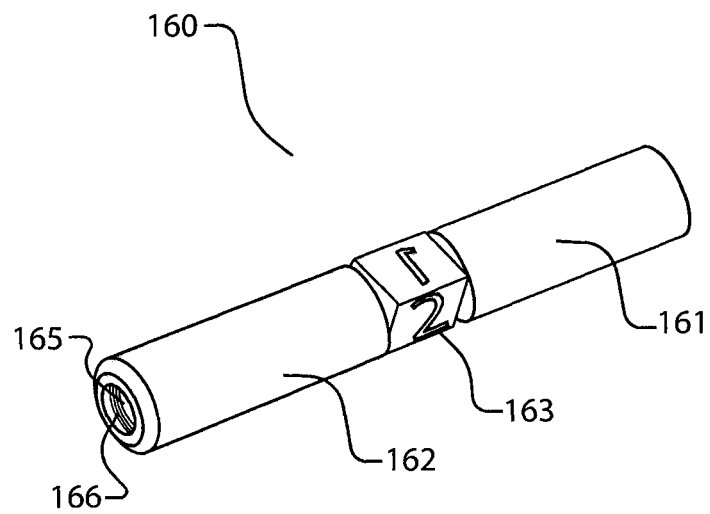
FIG. 6A is a perspective view of an alternative shuttle assembly that may be used according to principles described herein.
Figure 6B:
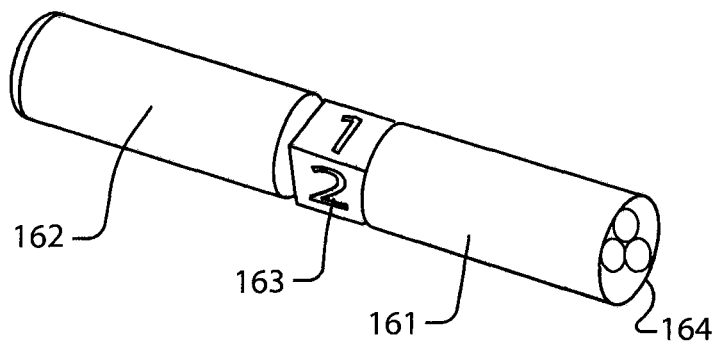
FIG. 6B is another perspective view of the shuttle assembly of FIG. 6A according to principles described herein.

FIG. 6A is a perspective view of an alternative shuttle assembly 160 that may be used in connection with the systems and methods described herein. FIG. 6B is another perspective view of the shuttle assembly 160 of FIG. 6A. As shown in FIGS. 6A-6B, the shuttle assembly 160 may include a proximal member 161, a distal member 162, and one or more identifying marks 163 disposed on the proximal member 161.

The proximal member 161 may include a plurality of receiving ports 164 configured to couple corresponding leads 101 to the shuttle assembly 160. For example, the proximal member 161 may include three receiving ports 164, as shown in FIG. 6B, for receiving three distinct leads 101. It will be recognized that the proximal member 161 may alternatively include any number of receiving ports 164 as may serve a particular application. The ports 164 may be similar to ports 122 described above and may include any coupling means configured to couple the leads 101 to the shuttle assembly 160.

The identifying marks 163 may be similar to the identifying marks 124 described above and may be configured to facilitate differentiation of the leads 101 after they have been coupled to the ports 164. The identifying marks 163 may include identifying numbers, colors, dots, stamps, ink, laser etchings, and/or any other suitable mark as may serve a particular application.

In some examples, the distal member 162 of the shuttle assembly 160 may be coupled to the proximal member 161 in a manner that allows the distal member 162 to rotate freely around a central axis extending along the length of the shuttle assembly 160. The distal member 162 may also include a receiving port 165 with internal threads 166 disposed therein. In this manner, as will be described in more detail below, the distal member 162 may be configured to removably couple to a tunneling rod.

Figure 7:
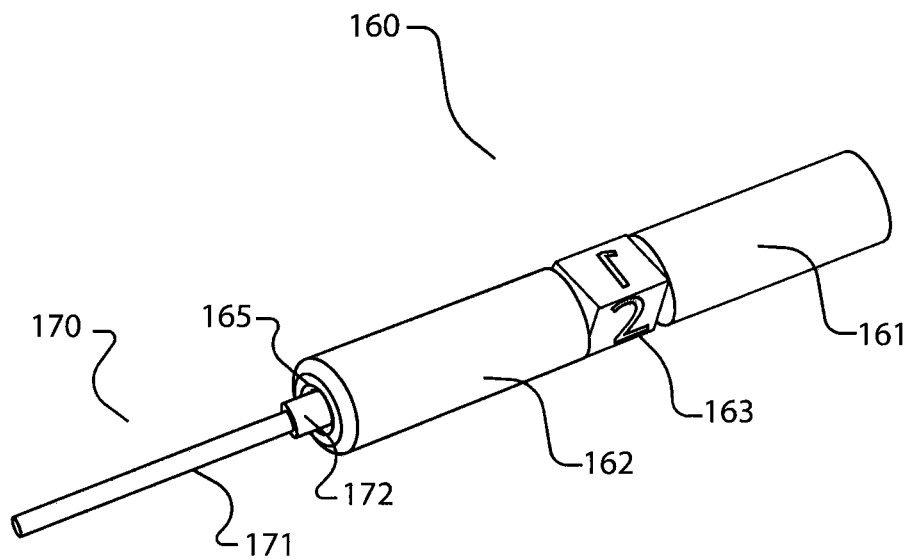
FIG. 7 illustrates a configuration wherein a shuttle assembly is coupled to a tunneling rod according to principles described herein.

FIG. 7 illustrates a configuration wherein the shuttle assembly 160 is coupled to a tunneling rod 170. The function of the tunneling rod 170 will be described in more detail below.

As shown in FIG. 7, the tunneling rod 170 may include an elongate shaft 171 and a coupling portion 172. The coupling portion 172 may be configured to fit within the receiving port 165 of the shuttle assembly 160 and may include threads configured to mate with the internal threads 166 of the receiving port 165. The distal member 162 may then be rotated until the tunneling rod 170 is securely coupled to the shuttle assembly 160. In this manner, the tunneling rod 170 may be coupled to the shuttle assembly 160 without twisting or manipulating the leads 101 that are attached to the shuttle assembly 160. It will be recognized that other coupling means may be used to couple the tunneling rod 170 to the shuttle assembly 160 as may serve a particular application.

The tunneling rod 170 may be configured to allow a user to pull the shuttle assembly 160 from the stimulation site to the implant site of the stimulator 100. For example, the tunneling rod 170 may be initially disposed within a tunneling straw. The tunneling straw and tunneling rod 170 may then be inserted into the patient and tunneled from the stimulation site to the implant site of the stimulator 100. The coupling portion 172 of the tunneling rod 170 may then be coupled to the shuttle assembly 160. The surgeon or other user may then pull the tunneling rod 170 and shuttle assembly 160 through the tunneling straw towards the implant site of the stimulator 100.

In some alternative examples, the tunneling rod 170 may be configured to create a tunnel in between the stimulation site and the implant site of the stimulator 100 before a tunneling straw is inserted within the tunnel. In this manner, tissue damage may be minimized by first creating a relatively small diameter tunnel with the tunneling rod 170 before expanding the diameter of tunnel with the tunneling straw.

Figure 8:
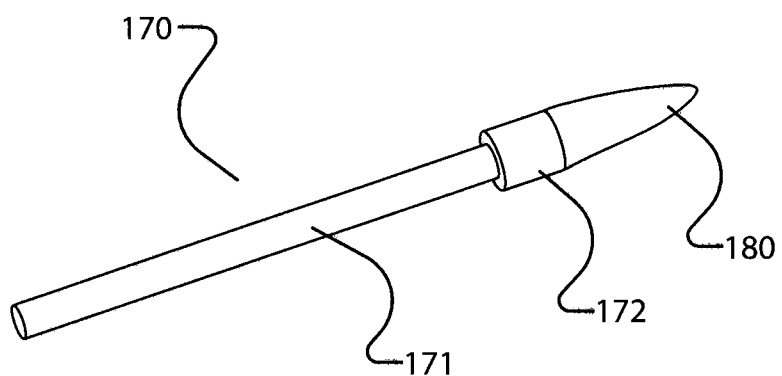
FIG. 8 illustrates a configuration wherein a tunneling rod is coupled to a tissue separator tip according to principles described herein.

To this end, the tunneling rod 170 may be removably coupled to a tissue separator tip. FIG. 8 illustrates a configuration wherein the tunneling rod 170 is coupled to a tissue separator tip 180. As shown in FIG. 8, the tissue separator tip 180 may be coupled to the coupling portion 172 of the tunneling rod 170. The tissue separator tip 180 is tapered to allow it to separate tissue as the tunneling rod 170 is tunneled in between the stimulation site and the implant site of the stimulator 100.

Figure 9:
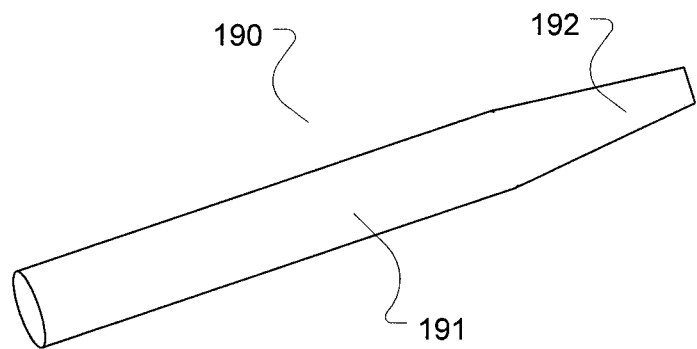
FIG. 9 illustrates an exemplary tunneling straw according to principles described herein.

After the tunneling rod 170 and tissue separator tip 180 have created an initial path or tunnel in between the stimulation site and the implant site of the stimulator 100, a tunneling straw may be inserted over the tunneling rod 170 such that the tunneling rod 170 is disposed within the lumen of the tunneling straw. In this manner, the diameter of the tunnel may be gradually expanded to a size configured to allow passage therethrough of the shuttle assembly 160. FIG. 9 illustrates an exemplary tunneling straw 190 that may be used in connection with the systems and methods described herein. It will be recognized that the tunneling straw 190 is merely illustrative of the many different types of tunneling straws that may be used in connection with the systems and methods described herein.

As shown in FIG. 9, the tunneling straw 190 may include a main portion 191 coupled to a tapered portion 192. The tapered portion 192 is configured to gradually expand the diameter of the tunnel by separating the tissue surrounding the tunnel as the tunneling straw 190 is inserted over the tunneling rod 170. In this manner, the tapered portion 192 is configured to prevent or minimize cutting of tissue.

In some examples, the smallest diameter of the tapered portion 190 may be configured to be slightly greater than the diameter of the tunneling rod 170 so as to allow the tunneling rod 170 to fit within the tunneling straw 190. The diameter of the main portion 191 may be configured to be slightly greater than the diameter of the shuttle assembly 160 so as to allow passage therethrough of the shuttle assembly 160.

Figure 10:
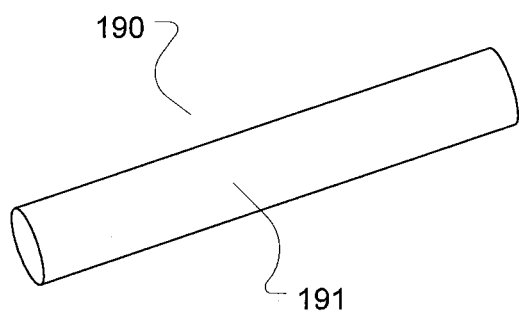
FIG. 10 shows the tunneling straw of FIG. 9 after the tapered portion has been removed therefrom according to principles described herein.

After the tunneling straw 190 is placed over the tunneling rod 170, a surgeon may cut or otherwise remove the tapered portion 192 from the tunneling straw 190. For example, FIG. 10 shows the tunneling straw 190 of FIG. 9 after the tapered portion 192 has been removed therefrom. By removing the tapered portion 192, the relatively large diameter shuttle assembly 160 may pass all the way through the lumen of the tunneling straw 190.

In some alternative examples, the end of the tunneling rod 170 opposite that of the coupling portion 172 may be configured to separate tissue in order to form a tunnel. In this manner, the shuttle assembly 160 may be coupled to the tunneling rod 170 before the tunneling rod 170 is inserted into the patient. As the tunneling rod 170 creates the tunnel in between the stimulation site and the implant site of the stimulator 100, the shuttle assembly 160 is passed from the stimulation site to the implant site of the stimulator 100 by virtue of being coupled to the tunneling rod 170. In this manner, use of a tunneling straw may be avoided.

Figure 11:
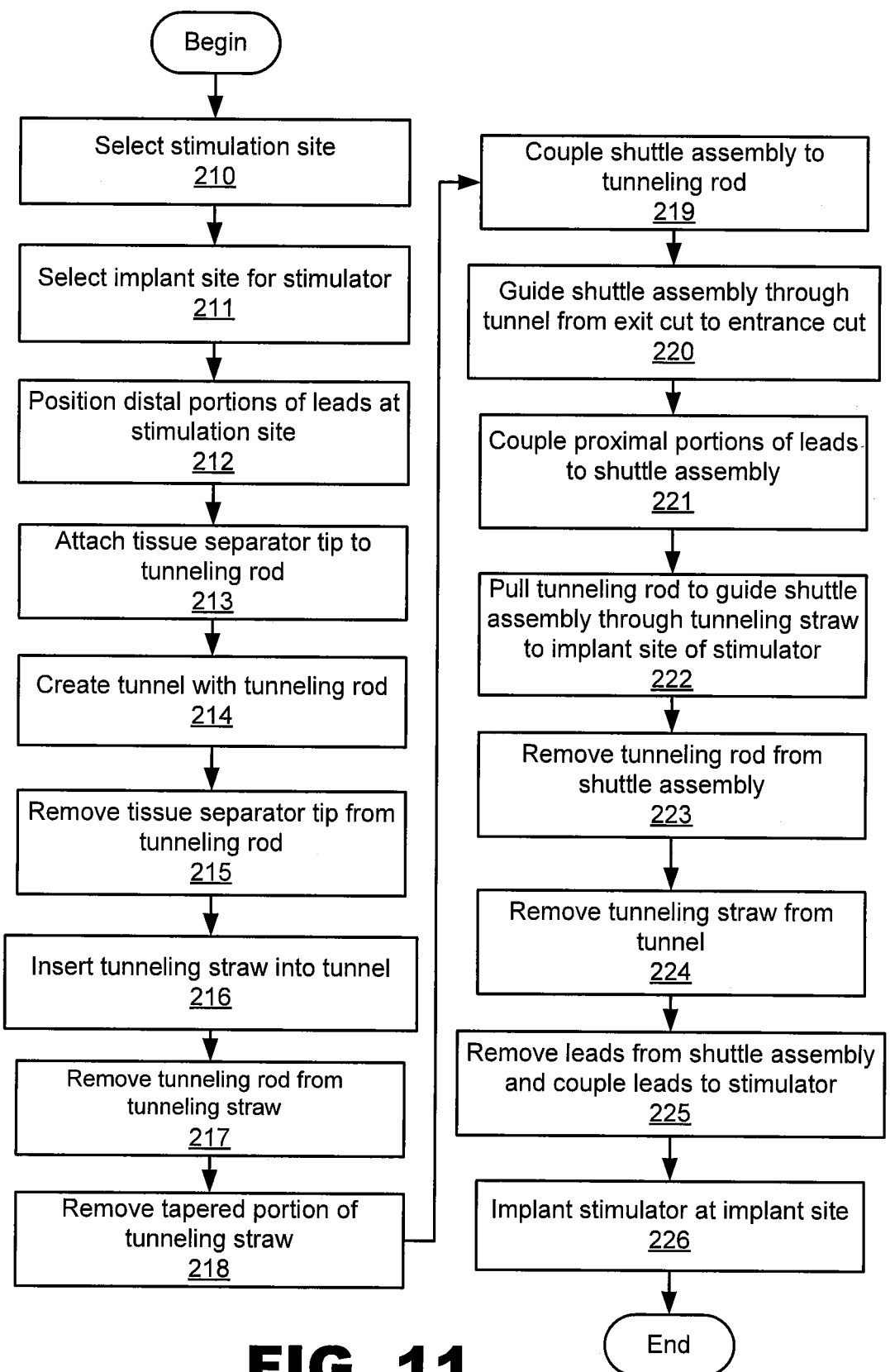
FIG. 11 is a flow chart illustrating an exemplary method of facilitating lead identification with the shuttle assembly of FIGS. 6A-6B according to principles described herein.

FIG. 11 is a flow chart illustrating an exemplary method of facilitating lead differentiation with a shuttle assembly similar to that described in connection with FIGS. 6A-6B. While FIG. 11 illustrates exemplary steps according to one embodiment, other embodiments may omit, add to, reorder, and/or modify any of the steps shown in FIG. 11.

In step 210, a stimulation site within a patient is selected. For example, the stimulation site may be located within the brain, the epidural space of the spinal cord, near a peripheral nerve, or at any other suitable location. An entrance cut may be made through the skin of the patient (e.g., with a scalpel) at a location that enables the surgeon to place stimulating leads at the stimulation site.

In step 211, an implant site for a stimulator is selected. The implant site may include any site within the patient as may serve a particular application. For example, the implant site may include a subcutaneous pocket created in the torso of the patient or any other surgically convenient location. An exit cut may be made through the skin of the patient at a location that enables the surgeon to placed the stimulator at the implant site.

In step 212, distal portions of the leads are positioned at the stimulation site such that the electrodes that are disposed thereon are in communication with the stimulation site.

In step 213, a tissue separator tip is coupled to a tunneling rod. In some alternative examples, the tunneling rod may be configured to be able to separate tissue without the use of a tissue separator tip.

In step 214, a tunnel in between the stimulation site and the implant site of the stimulator is created using the tunneling rod. In some examples, the tunnel may be created by inserting the end of the tunneling rod that has the tissue separator tip coupled thereto into the entrance cut made by the surgeon. The tunneling rod may then be guided towards the implant site of the stimulator until the end of the tunneling rod having the tissue separator tip coupled thereto exits through the exit cut made by the surgeon. In some alternative examples, the tunnel may be created by guiding the tunneling rod from the exit cut to the entrance cut. However, for illustrative purposes only, it will be assumed in this example that the tunneling rod is guided from the entrance cut to the exit cut.

In step 215, the tissue separator tip is removed from the tunneling rod while the tunneling rod is still within the tunnel. For example, the surgeon may unscrew or otherwise disengage the tissue separator tip from the tunneling rod.

In step 216, a tunneling straw is inserted into the tunnel and guided over the tunneling rod such that the tunneling rod is disposed within the lumen of the tunneling straw. In some examples, the tunneling straw is tapered at one end, as described above. In this manner, the diameter of the tunnel may be gradually increased as the tunneling straw is guided along the tunnel.

The tunneling straw may be inserted into the entrance cut and guided to the exit cut or vice versa, as may serve a particular application. In some examples, the tunneling straw is guided through the tunnel until a distal portion thereof (e.g., the tapered portion) exits either the entrance or exit cut. For example, if the tunneling straw is inserted into the entrance cut, it may be guided through the tunnel until a distal portion thereof exits the exit cut.

In step 217, the tunneling rod is removed from the tunneling straw.

In step 218, the tapered portion of the tunneling straw is removed. For example, the surgeon may cut off the tapered portion from the tunneling straw. In this manner, a shuttle assembly may later pass through the remaining portion of the tunneling straw.

In step 219, a shuttle assembly is coupled to the tunneling rod. The shuttle assembly may be coupled to the coupling portion of the tunneling rod that has exited the exit cut.

In step 220, the tunneling rod is used to guide the shuttle assembly through the tunnel from the exit cut to the entrance cut.

In step 221, proximal portions of a plurality of electrode leads are coupled to the shuttle assembly. The proximal portions of the leads may be coupled to the shuttle assembly in any of the ways described herein. For example, each lead may be coupled to a distinct port that is a part of the shuttle assembly. The shuttle assembly may also include a distinct identifier corresponding to each port.

In step 222, the tunneling rod is pulled from the implant side of the tunnel to guide the shuttle assembly through the tunneling straw to the implant site of the stimulator. Care may be taken to not dislodge the leads from the shuttle assembly.

In step 223, the tunneling rod is removed from the shuttle assembly after the shuttle assembly and proximal ends of the leads are on the implant side of the tunneling straw. For example, the surgeon may grasp the shuttle assembly after it has exited the tunneling straw and unscrew or otherwise remove the tunneling rod from the shuttle assembly.

In step 224, the tunneling straw is removed from the tunnel. For example, the surgeon may allow the shuttle assembly to go into the lumen of the tunneling straw as the straw is pulled from the tunnel and out of the exit cut. After the tunneling straw passes over the shuttle assembly and exits the tunnel completely, the tunneling straw may be discarded.

In step 225, the leads are removed from the shuttle assembly and coupled to the stimulator. In some examples, the leads are removed from the shuttle assembly and coupled to the stimulator one at a time. In this manner, the surgeon may differentiate the leads one from another as they are removed from the shuttle assembly by noting the identifying marks that are a part of the shuttle assembly.

In step 226, the stimulator is implanted at the selected implant site. Any suitable method of implantation may be used as may serve a particular application. The stimulator may then generate and apply electrical stimulation via one or more of the leads to the stimulation site.

Figure 12:
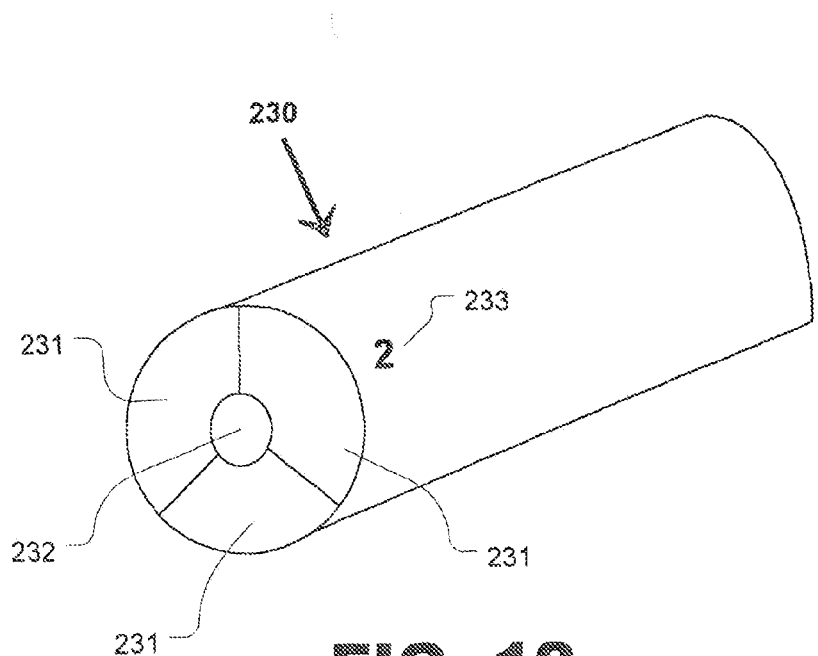
FIG. 12 illustrates an exemplary multi-lumen tunneling straw according to principles described herein.

In some examples, a multi-lumen tunneling straw may be used to facilitate differentiation of leads 101 after they have been routed from the stimulation site to the implant site of the stimulator 100. For example, FIG. 12 illustrates an exemplary multi-lumen tunneling straw 230 that may be used in accordance with the systems and methods described herein. The multi-lumen tunneling straw 230 may be made out of any suitable material as may serve a particular application. For example, the multi-lumen tunneling straw 230 may be made out of a plastic, polymer, metal, or any other material shown to be suitable for insertion within a patient.

As shown in FIG. 12, the multi-lumen tunneling straw 230 may include a plurality of lumens 231 extending therethrough. Each lumen 231 may be configured to allow passage therethrough of one of the leads 101. In this manner, the leads 101 may be separated one from another as they are guided from the stimulation site to the implant site of the stimulator 100. To this end, the multi-lumen tunneling straw 230 may include any number of lumens as may serve a particular application. For example, the tunneling straw 230 shown in FIG. 12 includes three lumens 231.

An additional lumen 232 may also be included within the tunneling straw 230. The additional lumen 232 may be configured to facilitate passage of one or more medical instruments such as a tunneling rod, guide wire, and/or any other instrument as may serve a particular application.

In some examples, one or more identifying marks 233 may be disposed on the tunneling straw 230 to identify each of the lumens 231. The identifying marks 233 may be similar to the identifying marks 124 described above.

Figure 13:
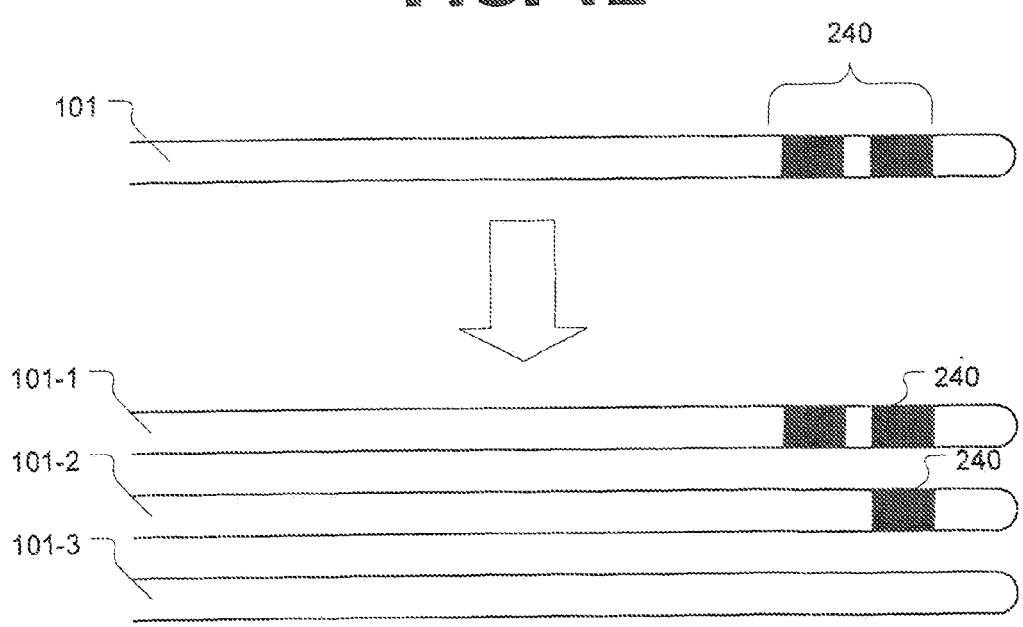
FIG. 13 shows a proximal portion of a number of leads having a number of bands disposed thereon according to principles described herein.

In some alternative examples, one or more identifying bands may be included on one or more of the leads 101 to facilitate differentiation thereof. For example, FIG. 13 shows a proximal portion of a lead 101 having a number of bands 240 disposed thereon. The bands may be made out of an elastic material or out of any other material as may serve a particular application.

In some examples, the bands 240 may be pre-loaded onto the leads 101 during manufacturing or at any other suitable time. For example, each lead 101 may be pre-loaded with two bands 240, as shown in FIG. 13. It will be recognized that any number of bands 240 may be loaded onto each of the leads 101 as may serve a particular application.

In some examples, one or more of the bands may be removed by the surgeon or other user to differentiate the leads 101 one from another. For example, if there are three leads 101-1 through 101-3 each with two pre-loaded bands 240 disposed thereon, a surgeon may remove one band 240 from one of the leads (e.g., 101-2) and both bands 240 from one of the leads (e.g., 101-3). In this manner, each of the leads 101 includes a different number of bands 240.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A system comprising:
   a stimulator configured to be implanted at an implant site within a patient and generate electrical stimulation current;
   a plurality of leads each comprising a proximal end, a distal end, and one or more electrodes disposed along the distal end and configured to deliver said electrical stimulation current at a stimulation site within said patient; and
   a shuttle assembly comprising a plurality of receiving ports formed as longitudinal grooves on an exterior surface of the shuttle assembly each groove configured to receive the proximal end of one of said leads and Guide said leads from said stimulation site to said implant site of said stimulator;
   wherein said shuttle assembly is configured to enable a user to differentiate between each of said leads after said leads are guided to said implant site of said stimulator, wherein said shuttle assembly is configured to be coupled to a tunneling rod, wherein said shuttle assembly comprises a proximal member and a distal member coupled to said proximal member, wherein said distal member comprises a receiving port configured to couple to said tunneling rod, wherein said distal member is configured to rotate freely, with respect to the proximal member, around a central axis.

2. The system of claim 1, wherein said shuttle assembly comprises at least one identifying mark configured to enable said user to differentiate between each of said leads.

3. The system of claim 1, wherein the proximal ends of said leads are configured to snap into said grooves.

4. The system of claim 1, further comprising a tunneling straw configured to receive said shuttle assembly and facilitate said guiding of said leads to said implant site of said stimulator.

5. The system of claim 1, wherein said implant site of said stimulator comprises a subcutaneous pocket formed within a torso of said patient.

6. A method comprising:
   providing the system of claim 1;
   implanting the stimulator of the system at an implant site within a patient;
   positioning said distal ends of said plurality of leads of the system at a stimulation site within said patient;
   coupling the proximal end of each of said leads into the longitudinal grooves of the shuttle assembly of the system; and
   guiding said shuttle assembly from said stimulation site to said implant site of said stimulator.

7. The method of claim 6, further comprising passing said shuttle assembly through a tunneling straw from said stimulation site to said implant site of said stimulator.

8. The method of claim 6, further comprising coupling said shuttle assembly to a tunneling rod.

9. The method of claim 8, further comprising using said tunneling rod to guide said shuttle assembly from said stimulation site to said implant site of said stimulator.

10. A system comprising:
    a stimulator configured to be implanted at an implant site within a patient and generate electrical stimulation current;
    a plurality of leads each comprising a proximal end, a distal end, and one or more electrodes disposed along the distal end and configured to deliver said electrical stimulation current at a stimulation site within said patient; and a shuttle assembly comprising a plurality of receiving ports formed as longitudinal grooves on an exterior surface of the shuttle assembly, each groove configured to receive the proximal end of one of said leads and guide said leads from said stimulation site to said implant site of said stimulator;

a tunneling rod configured to be removably coupleable to said shuttle assembly and create a tunnel between said stimulation site and said implant site; and a tunneling straw configured to be inserted within said tunnel;

wherein said tunneling rod is configured to guide said shuttle assembly through said tunneling straw from said stimulation site to said implant site of said stimulator;

wherein said shuttle assembly comprises a proximal member and a distal member coli led to said proximal member, wherein said distal member comprises a receiving port configured to couple to said tunneling rod, wherein said distal member is configured to rotate freely, with respect to the proximal member, around a central axis; and wherein said shuttle assembly is configured to enable a user to differentiate between each of said leads after said shuttle assembly is guided to said implant site of said stimulator.

11. The system of claim 10, wherein said shuttle assembly comprises at least one identifying mark configured to enable said user to differentiate between each of said leads.

12. The system of claim 10, wherein the proximal ends of said leads are configured to snap into said grooves.

13. The system of claim 10, wherein said tunneling rod is further configured to be removably coupleable to a tissue separator tip.

14. The system of claim 10, wherein said tunneling straw comprises a tapered portion configured to increase a diameter of said tunnel as said tunneling straw is inserted within said tunnel.

15. A method comprising:
providing the system of claim 10;
selecting a stimulation site;
selecting an implant site for Hull the stimulator of the system:
creating a tunnel in between said stimulation site and said implant site with the tunneling rod of the system;
inserting the tunneling straw of the system into said tunnel;
coupling the shuttle assembly of the system to said tunneling rod;
coupling the proximal end of each of the plurality of electrode leads of the system to corresponding ports formed as the longitudinal grooves of said shuttle assembly;
guiding said shuttle assembly through said tunneling straw from said stimulation site to said implant site with said tunneling rod;
removing said tunneling straw from said tunnel;
removing said leads from said shuttle assembly in a manner configured to distinguish each of said leads one from another; and
coupling each of said leads to said stimulator.

16. The method of claim 15 wherein said tunneling straw comprises a tapered portion.

17. An apparatus comprising:
an elongated body configured to be Guided from a stimulation site to an implant site of a stimulator within a patient;
a plurality of receiving ports formed as longitudinal grooves on an exterior surface of said elongated body and each groove configured to receive a proximal end of an electrode lead; and
at least one identifying mark configured to enable a user to differentiate between each of said leads after said elongated body is guided from said stimulation site to said implant site, wherein said elongated body is configured to be coupled to a tunneling rod, wherein said elongated body comprises a proximal member and a distal member coupled to said proximal member, wherein said distal member comprises a receiving port configured to couple to said tunneling rod, wherein said distal member is configured to rotate freely, with respect to the proximal member, around a central axis.

18. The apparatus of claim 17, wherein said elongated body is configured to pass through a tunneling straw.

19. The apparatus of claim 17, wherein said implant site of said stimulator comprises a subcutaneous pocket formed within a torso of said patient.

20. The apparatus of claim 17, wherein said identifying mark comprises at least one of a number, a dot, or a stamp.

21. The apparatus of claim 17, wherein the proximal ends of said leads are configured to snap into said grooves.

* * * * *